United States Patent [19]

Kearney

[11] Patent Number: 4,665,226

[45] Date of Patent: May 12, 1987

[54] PROCESS FOR PREPARING 5-(2,5-DIMETHYLPHENOXY)-2,2-DIMETHYLPENTANOIC ACID

[75] Inventor: Francis R. Kearney, Holland, Mich.

[73] Assignee: Warner-Lambert Company, Morris Plains, N.J.

[21] Appl. No.: 806,312

[22] Filed: Dec. 9, 1985

[51] Int. Cl.$^4$ .............................................. C07C 59/48
[52] U.S. Cl. ...................................... 562/471; 560/226
[58] Field of Search .......................................... 562/471

[56] References Cited

U.S. PATENT DOCUMENTS

| 3,674,836 | 7/1972 | Creger et al. | 562/471 |
| 3,707,566 | 12/1972 | Creger et al. | 562/471 |
| 3,759,986 | 9/1973 | Creger et al. | 562/471 |

OTHER PUBLICATIONS

Amer. J.Med., 5/23/83, pp. 23–27, "Effects of Gemfirgozil on Serum Lipids", P. Samuel.

Primary Examiner—Paul J. Killos
Attorney, Agent, or Firm—Jerry F. Janssen

[57] ABSTRACT

An improved two-step process for preparing 5-(2,5-dimethylphenoxy)-2,2-dimethylpentanoic acid (gemfibrozil) which regularly affords gembibrozil in overall yields in excess of 80% comprises reacting an alkali metal salt of a lower alkyl ester of 2-methylpropanoic acid with 1,3-dibromopropane or 1-bromo-3-chloropropane in a polar aprotic solvent such as tetrahydrofuran, and then reacting the intermediate thus formed with an alkali metal salt of 2,5-dimethylphenol in a mixed toluene/dimethylsulfoxide solvent system.

6 Claims, No Drawings

PROCESS FOR PREPARING 5-(2,5-DIMETHYLPHENOXY)-2,2-DIMETHYL-PENTANOIC ACID

BACKGROUND OF THE INVENTION

The present invention relates to chemical processes for preparing (substituted-phenoxy)alkanoic acids and esters. More particularly, the present invention concerns an improved process for preparing 5-(2,5-dimethylphenoxy)-2,2-dimethylpentanoic acid.

Substituted phenoxyalkanoic acids as a class have been found to regulate blood lipid levels and to possess utility as agents for the treatment or prevention of arteriosclerosis. (See, for example, U.S. Pats. Nos. 3,674,836 to Creger, 4,238,492 to Majoie, and 4,351,950 to Sircar.).

In particular, the compound 5-(2,5-dimethylphenoxy)-2,2-dimethylpentanoic acid, known generically as gemfibrozil, has been shown to be effective in elevating blood serum levels of high-density lipoproteins while simultaneously lowering the levels of low-density serum lipoproteins. (See, for example, P. Samuel, "Effects of Gemfibrozil on Serum Lipids", *Am. J. Med.*, May 23, 1983, pp. 23–27.

U.S. Pat. No. 3,674,836, discloses gemfibrozil and several analogues together with a process for their preparation.

U.S. Pat. No. 4,351,950 discloses phenylene-bis-alkoxyalkanoic acids and esters and two processes for their production.

SUMMARY OF THE INVENTION

In accordance with the present invention, a process for preparing 5-(2,5-dimethylphenoxy)-2,2-dimethylpentanoic acid (gemfibrozil) comprises the steps of: (a) reacting a lower alkyl ester of 2-methylpropanoic acid with an alkali metal salt of a di-(lower alkyl)amine in a polar aprotic organic solvent to produce an alkali metal salt of formula I

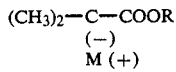

wherein R is lower alkyl and M is an alkali metal, and then with a 1,3-dihalopropane selected from 1-bromo-3-chloropropane and 1,3-dibromopropane at a temperature above about −20° C. to produce an intermediate of the formula

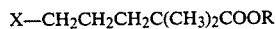

wherein X is chlorine or bromine and R is as defined above; (b) reacting said intermediate with an alkali metal salt of 2,5-dimethylphenol to produce 5-(2,5-dimethyphenoxy-2,2-dimethylpentanoic acid in yields greater than 80% from said lower alkyl ester of 2-methylpropanoic acid.

DETAILED DESCRIPTION

U.S. Pat. No. 3,674,836 teaches the preparation of 5-(2,5-dimethylphenoxy)-2,2-dimethylpentanoic acid (gemfibrozil) by a two step process in which 2,5-dimethylphenol is first O-alkylated with 1,3-dibromopropane to yield 1-(2,5-dimethylphenoxy)-3-bromopropane in accordance with the procedure described by Marvel et al., *Org. Synth.*, Collective Vol. I, pp 435–436, John Wiley & Sons, New York, 1941. Typical yields reported there for this reaction vary between 55–60%.

In the second step, the 1-(2,5-dimethylphenoxy)-3-bromopropane is reacted with the dianion of isobutyric acid, i.e.

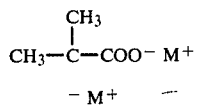

where M is an alkali metal ion, to give 5-(2,5-dimethylphenoxy)-2,2-dimethylpentanoic acid (gemfibrozil) in accordance with the procedure described by Creger in *Org. Synth.*, Vol. 50, pp. 58–62, John Wiley & Sons, New York, 1970. Typical yields reported there for this reaction vary between 70–76%. Thus, for this prior art process, typical overall yields range from a low of about 39% to a high of about 46%.

In contrast, the process of the present invention produces gemfibrozil from readily available starting materials in overall yields which regularly exceed 70%, frequently exceeding 80%. The process comprises first preparing a lower alkyl ester of 5-bromo- or 5-chloro-2,2-dimethylpentanoic acid when ester is then used to O-alkylate an alkali metal salt of 2,5-dimethylphenol.

In the first step of the present process, a lower alkyl ester of 2-methylpropanoic acid (isobutyric acid) is C-alkylated with either 1-bromo-3-chloropropane or 1,3-dibromopropane to yield the corresponding lower alkyl ester of 5-bromo- or 5-chloro-2,2-dimethylpentanoic acid. This step of the process involves the initial formation of an alkali metal salt of the carbanion at the tertiary carbon atom of the isobutyric acid ester followed by its alkylation with the 1,3-dihalopropane and is carried out in a single reaction vessel.

The term "lower ester" is intended to encompass alkyl ester groups of from one to four carbon atoms, including methyl, ethyl, n-propyl, isopropyl, n-butyl, sec-butyl, iso-butyl, and tert-butyl.

Higher yields are obtained from this alkylation step when the starting materials are the preferred ester, 2-methylpropyl 2-methylpropanoate (isobutyl isobutyrate) and the preferred dihalide 1-bromo-3-chloropropane.

This alkylation step of the process is carried out in an anhydrous polar aprotic organic solvent such as tetrahydrofuran, tetrahydropyran, dimethoxyethane, diethylene glycol dimethyl ether, and the like. The preferred solvent is tetrahydrofuran.

An alkali metal such as lithium or sodium is combined with the aprotic solvent, and a di-(lower alkyl)amine, followed by a conjugated olefin such as styrene, methyl styrene, isoprene, or naphthalene, to produce the corresponding alkali metal di(lower alkyl)amide. The preferred materials are lithium and diisopropylamine. The formation of the alkali metal di-(lower alkyl)amide is carried out at temperatures ranging from about 20° C. to about 60° C., with preferred temperatures lying in the range from about 30° C. to about 50° C.

The lower alkyl ester of 2-methylpropanoic acid is next added while maintaining the temperature of the reaction mixture between about −20° C. to about 20° C., preferably between about 5° C. to about 15° C. To this mixture is next added the 1-bromo-3-halo-propane, while still maintaining the temperature of the reaction mixture between about 0° C. and 20° C., preferably between about 5° C. and 15° C. The mixture is stirred for a period of from about 2 to about 15 hours, preferably about 12 hours after which the reaction is quenched by the addition of water, and the mixture is partitioned between water and a non-polar hydrocarbon solvent such as hexane. The organic phase is separated, optionally dried over an anhydrous dessicant such as magnesium sulfate, and the solvent removed. The residual lower alkyl ester of 5-bromo- or 5-chloro-2,2-dimethylpentanoic acid is purified by distillation.

Although either 1,3-dibromopropane or 1-bromo-3-chloropropane may be employed as the alkylating reagent in this step of the process, 1-bromo-3-chloropropane is preferred because of the higher yields that result. A comparison of the yields in employing the two materials is apparent from Examples 3 and 4. In Example 3, the preferred 1-bromo-3-chloropropane reagent was employed and the yield of methyl 5-chloro-2,2-dimethylpentanoate ester intermediate on a commercial scale was 81%. However, when the alternative 1,3-dibromopropane starting material was employed, as in Example 4, the yield of methyl 5-bromo-2,2-dimethylpentanoate on a comparable scale was only 67%. Formation of the undesired by-product formed from reaction of both bromine atoms of the 1,3-dibromopropane with two equivalents of the methyl lithioisobutyrate, which might otherwise be expected to diminish the yield of desired product, was minimized by "reverse addition" of the solution of the lithium salt to excess dibromide. In spite of this precaution, the yield of desired product was still lower than when the preferred 1-bromo-3-chloropropane starting material is employed.

As illustrated by Examples 2 and 3, the yield of the 5-chloro-2,2-dimethylpentanoate ester intermediate is greater when the preferred 2-methylpropyl 2-methylpropanoate (isobutyl isobutyrate) starting ester is employed. Thus, in Example 2, the yield of 2-methylpropyl 5-chloro-2,2-dimethylpentanoate was 94%, while use of the alternative starting ester, methyl 2-methylpropanoate (methyl isobutyrate) in Example 3 yielded only 81% of the desired intermediate.

In the second step of the process of this invention, 2,5-dimethylphenol is dissolved in a mixture of a higher-boiling non-polar hydrocarbon solvent and a polar solvent. The solution is then reacted with a strong base to produce the corresponding 2,5-dimethylphenolate salt. An alkali metal hydroxide such as sodium hydroxide or potassium hydroxide is preferred, and the mixture is heated under reflux with provision for the azeotropic removal of water from the reaction mixture as the 2,5-dimethylphenol is converted to the corresponding alkali metal phenolate. Although either sodium or potassium hydroxide may be employed, the preferred alkali metal hydroxide is sodium hydroxide because of its lower cost.

The alkali metal phenolate is then reacted with the 5-bromo- or 5-chloro-2,2-dimethylpentanoate ester to produce gemfibrozil. The reaction is generally carried out under reflux in the mixed solvent system for a period of from about 7 to about 20 hours. Suitable higher-boiling non-polar solvents include benzene, toluene and the xylenes, with toluene being preferred. Suitable polar solvents include dimethyl sulfoxide, dimethylformamide, dimethyl ether of ethylene glycol and similar ethers, with dimethyl sulfoxide being preferred.

The preferred mixed solvent system for this step of the reaction comprises from about 5 to about 15 parts (volume/volume) of toluene to one part dimethylsulfoxide. It has been found that in solvent systems employing ratios of toluene to dimethylsulfoxide greater than about 15:1 or less than 5:1, the yield of desired product falls off. More preferred ratios of toluene to dimethylsulfoxide lie in the range of about 5:1 to about 10:1, with optimum results being obtained with a ratio of toluene to dimethylsulfoxide at about 7.5:1.

As shown by Examples 5 and 6, a higher yield in this second step of the reaction is also obtained when the preferred intermediate 2-methylpropyl 5-chloro-2,2-dimethylpentanoate is employed. In Example 5, when this preferred intermediate was used, the yield of gemfibrozil was 92%, while the yield in Example 6 for this step was lowered to 86% when the corresponding methyl ester was employed.

Thus for the two step process of the present invention, overall yields of greater than 80% are realized as compared with considerably lower yields for the prior art process.

The following examples are provided to enable one skilled in the art to practice the invention. These examples are merely illustrative of the process of this invention and should not be read as limiting the scope of the invention as it is defined by the appended claims.

EXAMPLE 1

Preparation of Methyl
5-Chloro-2,2-dimethylpentanoate

Lithium metal shot (6.31 g, 0.91 mol) was weighed under an argon atmosphere and placed in an argon-filled 1-liter flask. Tetrahydrofuran (182 ml) and diisopropylamine (96.6 g, 0.955 mol) were added. The mixture was heated to 35° C. while styrene (48.8 g, 0.468 mol) was added slowly while maintaining the temperature between 35° C. and 42° C.

When the addition of styrene was complete, and the exotherm had subsided, the mixture was cooled and methyl isobutyrate (83.6 g, 0.819 mol) was added dropwise at 5° C. to 10° C.

Next, 1-bromo-3-chloropropane (193.7 g, 1.23 mol) was added at temperatures between 10° C. and 35° C. (mainly below 15° C.) and the mixture was allowed to warm to room temperature over a period of three days. The reaction mixture was then quenched by the addition of 40 ml of water, and the volume of the solution was reduced to 200 ml under vacuum. This residue was partitioned between 200 ml of hexane and 200 ml of water. The layers separated, and the aqueous layer was washed weith 100 ml of hexane. The combined organic layers were distilled and the product fraction collected at 56° C. to 62° C. (4 torr, 0.52 kPascal) to yield 107.7 g (74%) of methyl 5-chloro-2,2-dimethylpentanoate.

EXAMPLE 2

Preparation of 2-Methylpropyl
5-Chloro-2,2-dimethylpentanoate (Commercial Scale)

Employing, generally, the method of Example 1, 1.6 kg (0.230 kg-mol) of lithium metal was treated with 40.8 kg of dry tetrahydrofuran and 25.7 kg (0.254 kg-mol) of diisopropylamine followed by reaction with 12.68 kg (0.121 kg-mol) of styrene at temperatures between about 35°-40° C.

After reaction with the lithium metal was essentially complete, the mixture was cooled to temperatures between 5°–15° C. and 30 kg (0.208 kg-mol) of 2-methylpropyl 2-methylpropanoate (isobutyl isobutyrate) was slowly added.

The reaction mixture was again cooled to temperatures between about 5°–15° C. and 42.5 kg (0.270 kg-mol) of 1-bromo-3-chloropropane was slowly added. After addition was complete, the mixture was allowed to warm to 14° C. over a period of about 13 hours.

The final reaction mixture was quenched with 11.5 liters of water, the tetrahydrofuran removed, and the residue diluted with 75 liters of water and extracted with hexane. Removal of the hexane and distillation of the residue yielded 43 kg (0.195 kg-mol, 94%) of 2-methylpropyl 5-chloro-2,2-dimethylpentanoate, bp 94°–98° C. at 4 Torr (0.53 kPascal).

EXAMPLE 3

Preparation of Methyl 5-Chloro-2,2-dimethylpentanoate (Commercial Scale)

Employing, generally, the method of Example 2, 23.3 kg (0.218 kg-mol) of lithium diisopropylamide was prepared and reacted with 19.1 kg (0.187 kg-mol) of methyl 2-methylpropanoate (methyl isobutyrate) in tetrahydrofuran at temperatures between about 5°–15° C.

Reaction of the intermediate thus formed with 38.5 kg (0.244 kg-mol) of 1-bromo-3-chloropropane yielded, after work-up as described in Example 2, 27.1 kg (81%) of methyl 5-chloro-2,2-dimethylpentanoate, bp 72° C. at 6 torr (0.78 kPascal).

EXAMPLE 4

Preparation of Methyl 5-Bromo-2,2-dimethylpentanoate

Employing, generally, the method of Example 3, a tetrahydrofuran solution of 179.4 kg (1.66 kg-mol) of the lithium salt of methyl 2-methylpropanoate (methyl lithioisobutyrate) was added to 501 kg (2.48 kg-mol) of 1,3-dibromopropane, maintaining the temperature of the reaction mixture at temperatures between about 0°–10° C. After the reaction was complete, the mixture was stirred for 48 hours.

The reaction was then quenched by the addition of water, and the tetrahydrofuran was stripped from the mixture. The residue was partitioned between 600 liters of water and 80 kg of dichloromethane and acidified with hydrochloric acid. The water layer was extracted with 133 kg of dichloromethane and the combined organic layers were distilled to yield 248 kg (67%) of methyl 5-bromo-2,2-dimethylpentanoate, bp 60°–65° C. at 1 torr (0.13 kPascal).

EXAMPLE 5

Preparation of 5-(2,5-Dimethylphenoxy-2,2-dimethylpentanoci Acid (Starting with 2-Methylpropyl 5-Chloro-2,2-dimethylpentanoate)

To a solution of 21.99 kg (0.180 kg-mol) of 2,5-dimethylphenol in 135 liters of toluene and 18 liters of dimethylsulfoxide were added 7.8 kg (0.195 kg-mol) of sodium hydroxide. The mixture was heated under reflux until all of the water had been azeotropically removed, and 2.83 kg (0.019 kg-mol) of sodium iodide were added.

2-Methylpropyl 5-chloro-2,2-dimethylpentanoate (41.73 kg, 0.189 kg-mol) were added. The mixture was heated under reflux for an additional 13 hours, after which time 14.4 kg of sodium hydroxide were added and heating was continued for 4 hours.

The toluene was removed by distillation, the crude product was partitioned between 90 liters of water and 30 liters of hexane, and the aqueous layer was acidified with hydrochloric acid to yield crude 5-(2,5-dimethylphenoxy)-2,2-dimethylpentanoic acid (gemfibrozil). Recrystallization from aqueous methanol solution yielded 41.5 kg (92%).

EXAMPLE 6

Preparation of 5-(2,5-Dimethylphenoxy)-2,2-dimethylpentanoic Acid (Alternative Method Starting with Methyl 5-Chloro-2,2-dimethylpentanoate)

Employing, generally, the method of Example 5, 12.22 kg (0.100 kg-mol) of 2,5-dimethylphenol were reacted with 18.76 kg (0.091 kg-mol) of methyl 5-chloro-2,2-dimethylpentanoate. The yield of 5-(2,5-dimethylphenoxy)-2,2-dimethylpentanoic acid (gemfibrozil) was 21.6 kg (86%).

I claim:

1. A process for preparing 5-(2,5-dimethylphenoxy)-2,2-dimethylpentanoic acid comprising the steps of:
   (a) reacting 2-methylpropanoic acid, 2-methylpropyl ester with an alkali metal salt of a di-(lower alkyl)amine in a polar aprotic organic solvent to produce an alkali metal salt of formula I

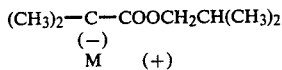

wherein M is an alkali metal, and then with 1-bromo-3-chloropropane at a temperature above about −20° C. to produce an intermediate of the formula

(b) reacting said intermediate with an alkali metal salt of 2,5-dimethylphenol to produce 5-(2,5-dimethylphenoxy)-2,2-dimethylpentanoic acid.

2. The process in accordance with claim 1 wherein step (c) is carried out at reflux temperatures in a mixed solvent system of a non-polar hydrocarbon solvent and a polar solvent.

3. The process in accordance with claim 2 wherein said mixed solvent system comprises from 5 parts (V/V) toluene to 1 part (V/V) dimethylsulfoxide to about 10 parts (V/V) toluene to 1 part (V/V) dimethylsulfoxide.

4. The process in accordance with claim 2 wherein said mixed solvent system comprises about 7.5 parts (V/V) toluene to 1 part (V/V) dimethylsulfoxide.

5. A process for preparing 5-(2,5-dimethylphenoxy)-2,2-dimethylpentanoic acid comprising the steps of:
   (a) reacting 2-methylpropyl 2-methylpropanoate with lithium diisopropylamide and then with 1-bromo-3-chloropropane at a temperature below about 25° C. to produce 2-methylpropyl 5-chloro-2,2-dimethylpentanoate
   (b) subsequently reacting said 2-methylpropyl 5-chloro-2,2-dimethylpentanoate with sodium 2,5-dimethylphenolate under reflux in a solvent comprising a mixture of from 10 parts (V/V) toluene/1 part (V/V) dimethylsulfoxide to 5 parts (V/V) toluene/1 part (V/V) dimethylsulfoxide, hydrolyzing the resulting ester, and thereafter acidifying the mixture and isolating 5-(2,5-dimethylphenoxy)-2,2-dimethylpentanoic acid;

whereby said 5-(2,5-dimethylphenoxy)-2,2-dimethylpentanoic acid is obtained in overall yield of greater than 80%.

6. The process of claim 5 wherein said solvent comprises a mixture of about 7.5 parts (V/V) toluene to 1 part (V/V) dimethylsulfoxide.

* * * * *